United States Patent [19]

Murphy-Chutorian

[11] Patent Number: 4,993,412
[45] Date of Patent: Feb. 19, 1991

[54] METHOD AND APPARATUS FOR REMOVAL OF OBSTRUCTIVE SUBSTANCE FROM BODY CHANNELS

[75] Inventor: Douglas R. Murphy-Chutorian, Palo Alto, Calif.

[73] Assignee: Eclipse Surgical Technologies, Inc., Mountain View, Calif.

[21] Appl. No.: 388,685

[22] Filed: Aug. 2, 1989

[51] Int. Cl.⁵ ............................................. A61B 17/36
[52] U.S. Cl. ...................... 606/7; 606/194; 128/398
[58] Field of Search ........................... 606/1–3, 606/7, 8, 14–17, 194; 128/303.1, 395–398; 604/96, 95

[56] References Cited

U.S. PATENT DOCUMENTS

| | | | |
|---|---|---|---|
| 4,669,467 | 6/1987 | Willett et al. | 606/7 |
| 4,781,681 | 11/1988 | Sharrow et al. | 606/7 X |
| 4,799,479 | 1/1989 | Spears | 606/7 |
| 4,819,632 | 4/1989 | Davies | 606/7 |
| 4,834,093 | 5/1989 | Littleford et al. | 606/7 |
| 4,854,315 | 8/1989 | Stack et al. | 128/398 X |

Primary Examiner—Robert A. Hafer
Assistant Examiner—Kerry Owens
Attorney, Agent, or Firm—Owen, Wickersham & Erickson

[57] ABSTRACT

A catheter device and a method for using same to facilitate removal of obstructive material in a human body channel. The catheter comprises an elongated body with a distal end portion adapted to be inserted within the channel and a proximal end portion. A lumen, extending lengthwise through said catheter body, supports a guidewire having a distal end along which the catheter body can be moved within the channel. A series of parallel, closely spaced fiber members extend through the catheter body from its proximal end and terminate near a distal end face of said catheter. Laser energy supplied at the catheter's proximal end is transmitted along the fiber members and is emitted forwardly therefrom at the catheter's distal end face. In one embodiment the catheter has a tapered nose portion for displacing obstructive material in the body channel before the emission of laser energy. In another embodiment, the fiber members are movable longitudinally in unison to sever and trap obstructive material which is removed from the body channel.

17 Claims, 7 Drawing Sheets

METHOD AND APPARATUS FOR REMOVAL OF OBSTRUCTIVE SUBSTANCE FROM BODY CHANNELS

This invention relates to methods and apparatus for removing substances or matter which cause obstructions, blockages or occlusions in body passages, channels or ducts such as arteries or veins.

BACKGROUND OF THE INVENTION

Although body channel obstructions such as blocked arteries have been treated heretofore using surgical arteriotomy techniques as well as with medicines for dissolving certain obstructive substances, a substantial effort has been made to perfect so-called minimally invasive techniques using catheter-based systems. In such systems, the artery is entered at a site remote from the obstruction so that elongated devices can be guided through the arterial system to the desired site. Such devices have included a catheter with a tapered tip which was pushed through the area of obstruction using a so-called Dotter technique or a catheter with an inflatable balloon near its distal tip for using the balloon angioplasty technique.

Other mechanical means of opening arteries include the use of rapidly rotating elements, for example the "Auth" technique which is an elongated device with a rotating diamond studded tip which grinds the obstructing material as it advances within the artery, or the "Fischell" technique which slices the blockage as it is withdrawn from the artery, or the "Stack" or Kensey techniques "Simpson" which use elongated catheters with rotating blades to chop the obstructing material, or the "Simpson" which is an elongated catheter that slices the obstruction at the side of the distal tip of the device.

Thermal and laser energy have also been used to open obstructed arteries. The "hot tip" technique utilizes thermal energy generated by electrical, chemical or laser to heat the tip of an elongated catheter which then vaporizes or melts the area of obstruction as it is advanced through the artery. Direct laser energy can be transmitted through elongated fiberoptic catheters to the site of obstruction in order to vaporize the obstruction.

To date, the mechanical means of removing obstructions from arteries are associated with formation of debris which flows downstream and blocks more distal vessels or with high frequency of closure of the artery after the procedure ranging from 25% to 50% in the case of the Auth, Simpson, balloon angioplasty, and related techniques. The cause of the reclosure is thought to be related to the mechanical damage to underlying healthy tissue and to the internal surface characteristics produced by the mechanical procedures. Attempts have been made to use laser energy or thermal energy after the mechanical techniques to improve the damaged surface characteristics and to weld any defects in the artery wall caused by the initial mechanical procedures.

Attempts have also been made to combine the use of laser energy with an angioplasty catheter to remove arterial obstructions as disclosed by Leckrone in U.S. Pat. Nos. 4,685,458 and 4,747,405. In these patents, a catheter having an attached inflatable balloon is provided with laser transmission filaments for ablating or dissolving obstructive material in an arterial passage.

One object of the present invention is to provide an improved catheter device for treating obstructions or blockages in body channels which combines the use of mechanical force thereof for displacing or compressing blockage material and manipulations with laser energy for dissolving or severing the blockage material.

Another object of the invention is to provide a catheter device for removing obstructions in body channels that enables the use of a reduced amount of laser energy directed so as to sever rather than dissolve the obstructing material, thereby reducing the danger of damaging healthy bodily tissue.

Another object of the invention is to provide a catheter device for removing obstructions in body channels that enables particles of removed obstructive material in body channels such as arteries to be trapped and retrieved, rather than allowed to fall into the fluid stream of the body channel.

Yet another object of the invention is to provide a catheter device for removing obstructions in body channels that is readily controllable and maneuverable in use to provide for efficient removal of body channel obstructions without damage to healthy tissue and thus with minimum risk to the patient.

SUMMARY OF THE INVENTION

In accordance with the principles of the present invention both mechanical and laser elements are combined in a catheter type device to dissolve, breakup and remove obstructive material from various body channels. Moreover, the removal process with my device may be accomplished with a minimal risk to healthy body components such as artery walls because the laser energy is directed so as to reduce the force required to remove obstructive material or to stretch the artery under treatment. Lower force requirements in expanding an opening in an arterial channel result in less damage to surrounding healthy tissues, and the laser simultaneously treats the internal arterial surface to achieve a smoother arterial lumen.

In general, a catheter device embodying principles of the invention comprises an elongated catheter body having a first lumen along its length for accommodating a movable, flexible guidewire of the conventional type. Also within the catheter body are a series of parallel, laser transmitting glass fibers. At or near the distal end of the catheter body the ends of these fibers are arranged fairly close together in a circular or arcuate pattern. At the proximal end of the catheter body the fibers are bunched together to interface with a laser generator in the conventional manner. In one embodiment of the invention a tapered or conical nose member is provided at the distal end of the catheter body which is axially aligned therewith inside a circular pattern of fiber ends. In use, the nose member forces obstructive material radially toward the walls of the body channel as the catheter is moved progressively into position at a blockage site. When the annular array of fibers is directly adjacent the obstruction material, laser energy form the fibers is provided with sufficient intensity to dissolve the obstructive material.

In a second embodiment, the guidewire is provided with an expandable element such as a balloon at its distal end so that it can be moved past an obstruction and then inflated. Again, an annular array of fibers in the catheter body is moved along the guidewire until it is directly adjacent to the obstructive material. Now, as laser energy is directed from the ends of the fibers, the catheter body moves closer to the balloon and most of the dissolved or broken off particles of the obstruction are trapped by the expandable element in the hollow end of the catheter so that they can be retrieved without falling into the body channel fluid.

A third embodiment of the invention provides a catheter body having a tapered distal end portion directly adjacent an open side compartment formed by inner and outer transverse faces. The inner transverse face has a series of arcuately arrayed laser transmitting fibers and these fibers are controllable at the proximal end of the catheter so as to be movable forwardly in unison from the inner transverse face to the outer transverse face of the catheter compartment. Thus, in use, a guidewire with an expandable element is first placed across the blockage and is expanded. The guidewire is then used to position the catheter directly opposite an accumulation or growth of obstructive material so that the material extends into the open catheter compartment. Now, as laser energy is directed from the ends of the fibers, the fibers are moved forwardly in unison toward the outer face of the compartment, effectively severing the main portion of the obstructive material. The moving fibers essentially serve as a gate which traps the severed material in the catheter compartment so that it can then be removed either when the catheter is withdrawn or by applying motion to an inner lumen of the catheter at its proximal end.

Other objects, advantages and features of the invention will become apparent from the following detailed description of the embodiments which is presented in conjunction with the accompanying drawing.

DETAILED DESCRIPTION OF EMBODIMENTS

In broad terms, the present invention provides a catheter device adapted to be moved through a body channel while using a combination of mechanical force and laser energy to remove, dissolve and/or retrieve obstructive material in the channel. Such body channels may be arteries, veins, ducts or passages although the following description of embodiments will refer primarily to use of the invention in arteries for the removal of plaque deposits.

With reference to the drawing, a first catheter device 10, embodying principles of the invention is shown in FIGS. 1A and 2A-2D. In general, this embodiment comprises a cylindrical catheter body 12 of a suitable flexible plastic material (e.g. polyethylene) having a uniform diameter along its length. Circumferentially spaced near its outer surface are a plurality of lumens 13 containing laser transmitting elements 14. These laser elements may be glass fibers having a diameter in the range of one to six hundred microns each. At the distal end of catheter 10, the exposed ends of the elements 14 are close together or contiguous and thus terminate at equally spaced apart intervals of less than the diameter of a fiber element around an annular end face 16. The elements thus form an annular ring which encircles the inner end of a conical nose member 18 on the catheter 10. This nose member may be of the same material as the catheter body and for best results, it has a length that is approximately three or four times the maximum diameter at its inner end. The nose member is either attached to or is made as an extended integral part of the catheter 10. Extending through the nose member and the entire length of the catheter is a central lumen 20 within which a conventional, movable guidewire 22 is supported. As shown in FIG. 3A, the catheter body may have an annular configuration with a central guidewire lumen 20 that is concentrically supported within the catheter body by internal transverse web members 24, or the catheter body may be essentially a solid member with appropriate lumen passages for the guidewire and the laser transmitting elements 14.

Figure 2A:
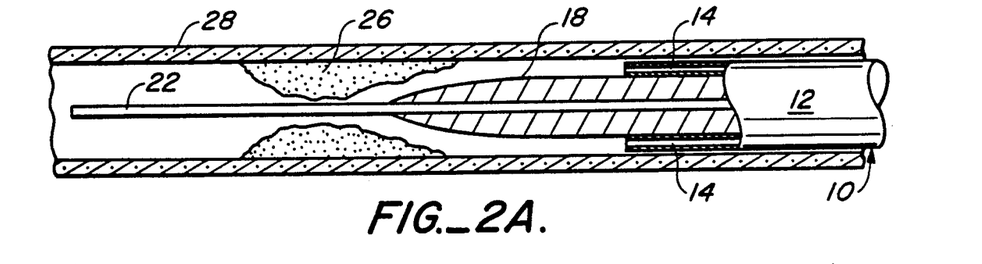
FIGS. 2A-2D are a series of elevation views in section showing the device of FIG. 1 in a typical operation within a body channel.
Figure 2B:
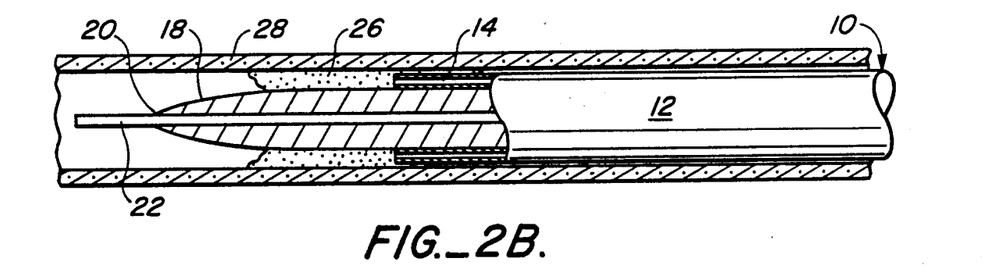
Figure 2C:
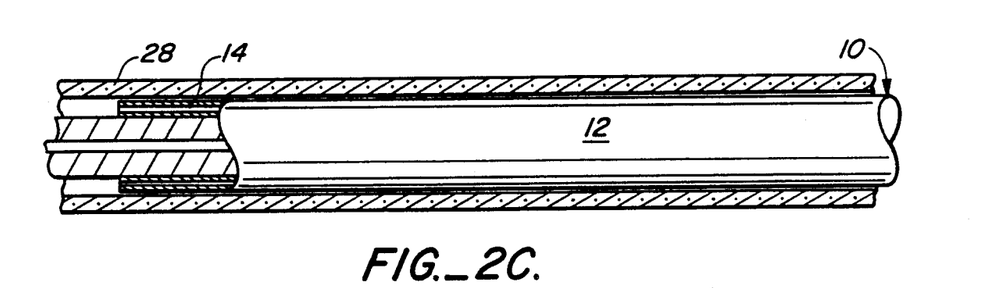
Figure 2D:
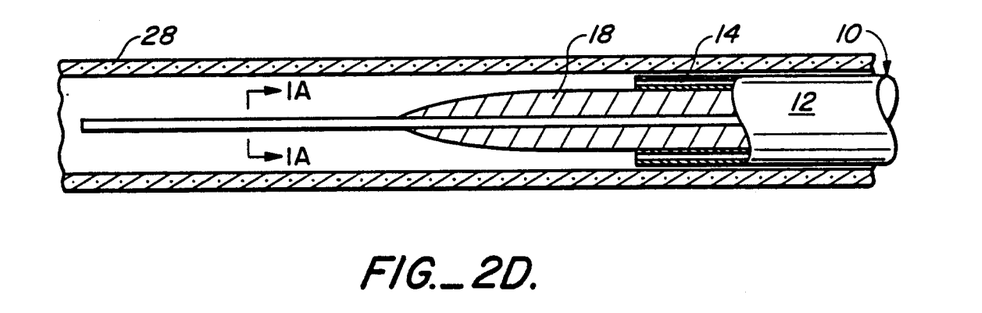
Figure 3A:
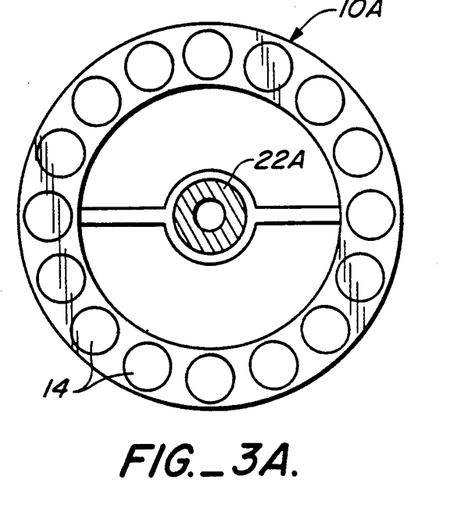
FIG. 3A is an enlarged view in section of the embodiment of FIG. 3, taken along the line 3A—3A of FIG. 4A.

A typical operation using the catheter 10 for removing an obstruction 26 in a lumen body channel 28 is illustrated in FIGS. 2A-2D. In many instances, the body channel will be an artery and the obstruction 26 is typically an accumulation of plaque. As a first step in the operative procedure, the guidewire 22 is inserted into the patient's body channel or artery 28 and using conventional fluoroscopic procedures, its distal end is moved through and beyond the obstruction 26. Now, the catheter 10 is installed around the guidewire 22 and is moved along it through the artery until its nose member 18 reaches the obstruction, as shown in FIG. 2A. At this point, a somewhat increased axial force is applied to the catheter, if necessary, in order to push well into the obstruction zone so that the ends of the glass fibers 14 are relatively close to the obstruction material. As shown in FIG. 2B, the nose member may actually push the obstruction material radially outwardly and compress it slightly so that it is compacted directly in front of the fiber ends 14. The tapered nose member allows this to be done with minimal stretching of the artery wall. Now, with the catheter positioned as shown in FIG. 2B, the laser energy source at the proximal end of the catheter is activated, preferably in a series of pulses, so that laser energy is transmitted from the fiber ends directly into the obstructive material. As the laser energy continues, the obstructive material is dissolved, and the catheter is constantly moved forward at a slow, but sustained rate until the obstruction is substantially fully dissolved. The catheter can then be withdrawn from the patient followed by retraction of the guidewire.

Figures 1, 3:
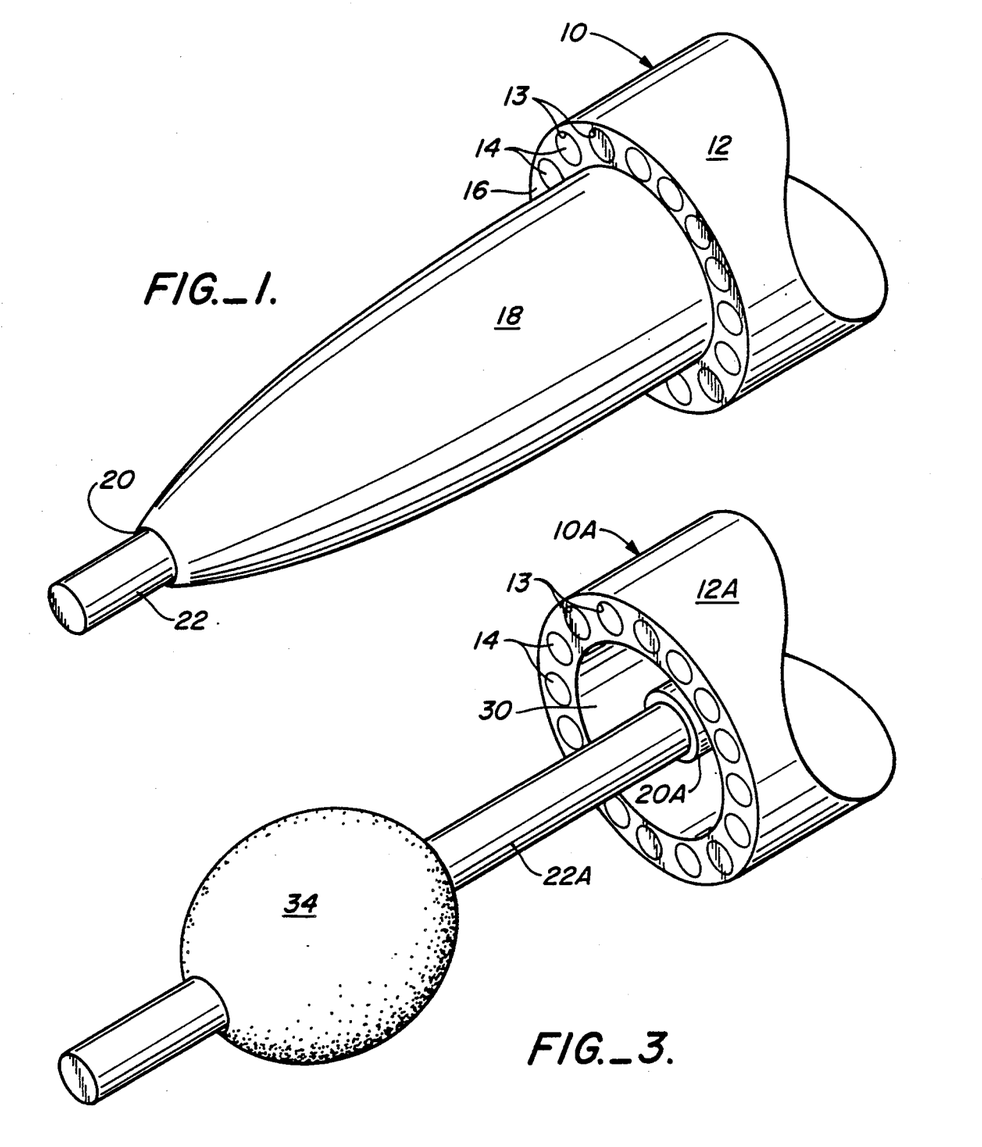
FIG. 1 is an enlarged fragmentary view in perspective showing the distal end of one form of catheter device according to the inventor.
FIG. 3 is an enlarged fragmentary view in perspective showing the distal end of another form of catheter device according to the invention.
Figure 1A:
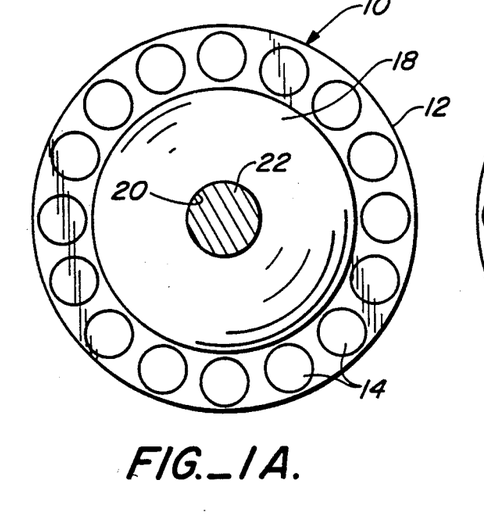
FIG. 1A is a front end view of the device shown in FIG. 1 and taken along line 1A—1A of FIG. D.

A modified form of catheter 10A embodying principles of the present invention is shown in FIG. 3. This catheter also has an annular body 12A surrounding a central bore 30 with a series of laser transmitting fibers 14 circumferentially, closely spaced near its outer surface, all of which terminate around an annular face 16 at its distal end. A central lumen 20A as described is provided within the central bore 30 of the catheter body for supporting a guidewire 22A. Here, as shown in FIG. 3A, the guidewire is of the type having an air conduit 32 or some suitable mechanism along its length which may be connected to either an inflatable balloon 34 or to some mechanically expandable element near the distal end of the guidewire. The balloon, if used, is of a size which is inflatable to a diameter slightly larger than the central bore 30 of the catheter body.

Figure 3B:
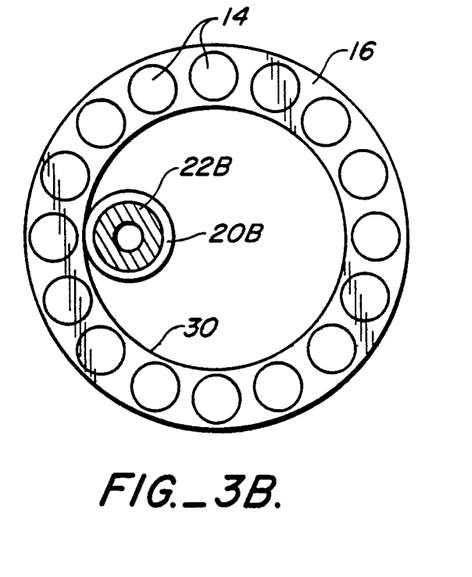
FIG. 3B is an enlarged view in section of the embodiment of FIG. 3, having an off-center guidewire lumen.

If desired, a lumen 20A for supporting the guidewire 22A may be attached off-center to one side of the catheter body vase 30, as shown in FIG. 3B. This arrangement provides an increased degree of maneuverability for the catheter, particularly where it is desired to move it closer to one side of a body channel.

Figure 9:
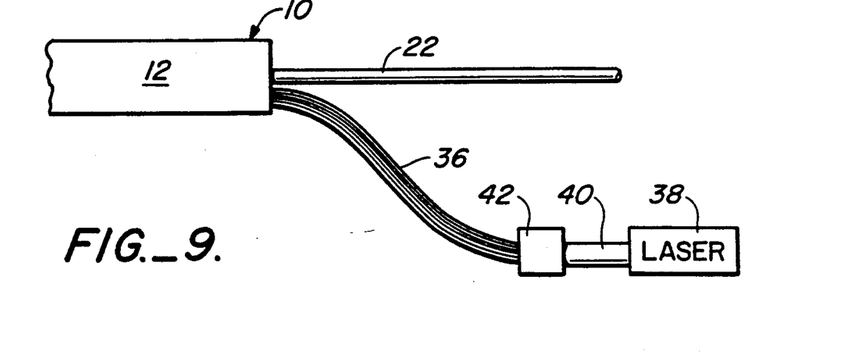
FIG. 9 is a view in section showing the proximal end for a catheter device according to the invention.

At or near the proximal end of the catheter body 10 and 10A the glass fibers 14 which are separate, but closely spaced at the distal end of the catheter body, are brought together in one fiber bundle 36. A laser transmission system is then used, as shown in FIG. 9 to transmit laser energy from a suitable generator source 38 through a single transmission element 40 and a connector 42 into the bundle of fibers and thence through the separate fibers 14 within the catheter body 12. Extending beyond the proximal end of the catheter body is the movable, controllable guidewire 22.

Figure 4A:
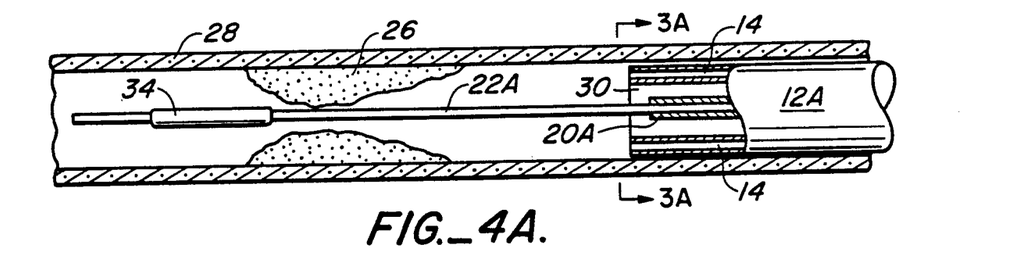
FIGS. 4A-4E are a series of elevation views in section showing the embodiment of FIG. 3 in a typical operation within a body channel.
Figure 4B:
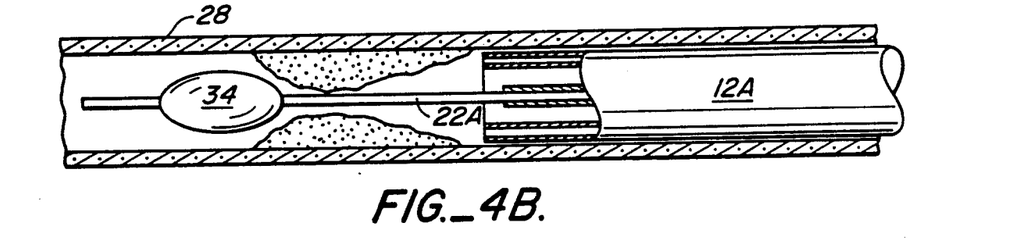
Figure 4C:
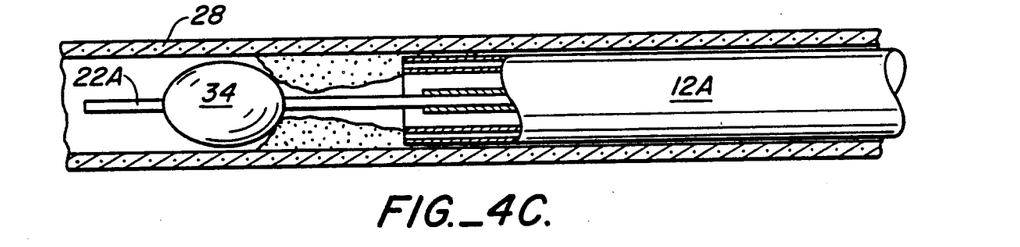
Figure 4D:
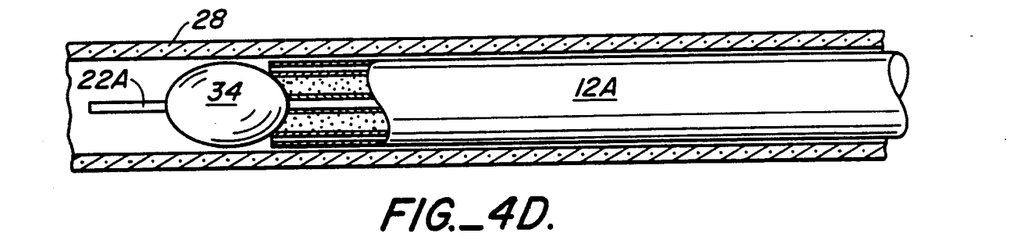
Figure 4E:
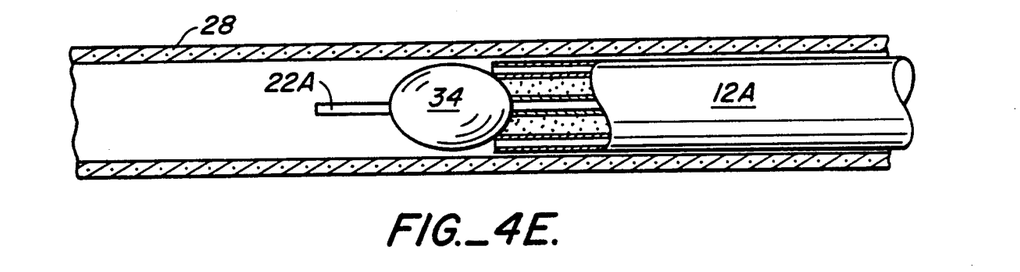

A typical operation utilizing the catheter 10A in a human artery having a blockage or obstruction 26 is shown in the FIGS. 4A–4E. As previously described relative to catheter 10, the guidewire 22A having an expandable element such as a balloon 34 near its distal end is moved through the artery 28 being treated to a point just beyond the obstruction 26. The balloon on the guidewire is now inflated to a diameter somewhat less than the artery diameter but greater than the opening through the arterial obstruction. Now, the catheter is installed around the guidewire at its proximal end and is moved along it through the artery until its annular end face is directly adjacent the obstruction material (FIG. 4B). As the catheter is continuously forced forwardly at a slow rate the laser energy source at its proximal end is activated. Laser energy thus passes through the fibers 14 and exits from its annular end face 16 directly upon the obstructive material (e.g. plaque), as shown in FIG. 4C. As the distal end of the catheter 10A is moved forwardly through the obstructive material, its end face 16 moves closer to the inflated balloon. Although a portion of the obstructive material is dissolved by the laser energy, the multiple laser beams from the cylindrical pattern of closely spaced fibers 14 may actually sever portions of the obstructive material 26 from the artery wall. Thus, as the balloon 34 moves closer to the end of the catheter it may force a larger portion of obstructive material directly into the open bore 30 at the end of the catheter body, as in FIG. 4D. Now, when the catheter body 10A and the guidewire 22A are removed together from the artery, the severed portions of obstructive material remain within the catheter and are also removed form the artery, thereby eliminating or greatly reducing any loose obstructive material from the blood flow in the artery.

Figures 5, 7:
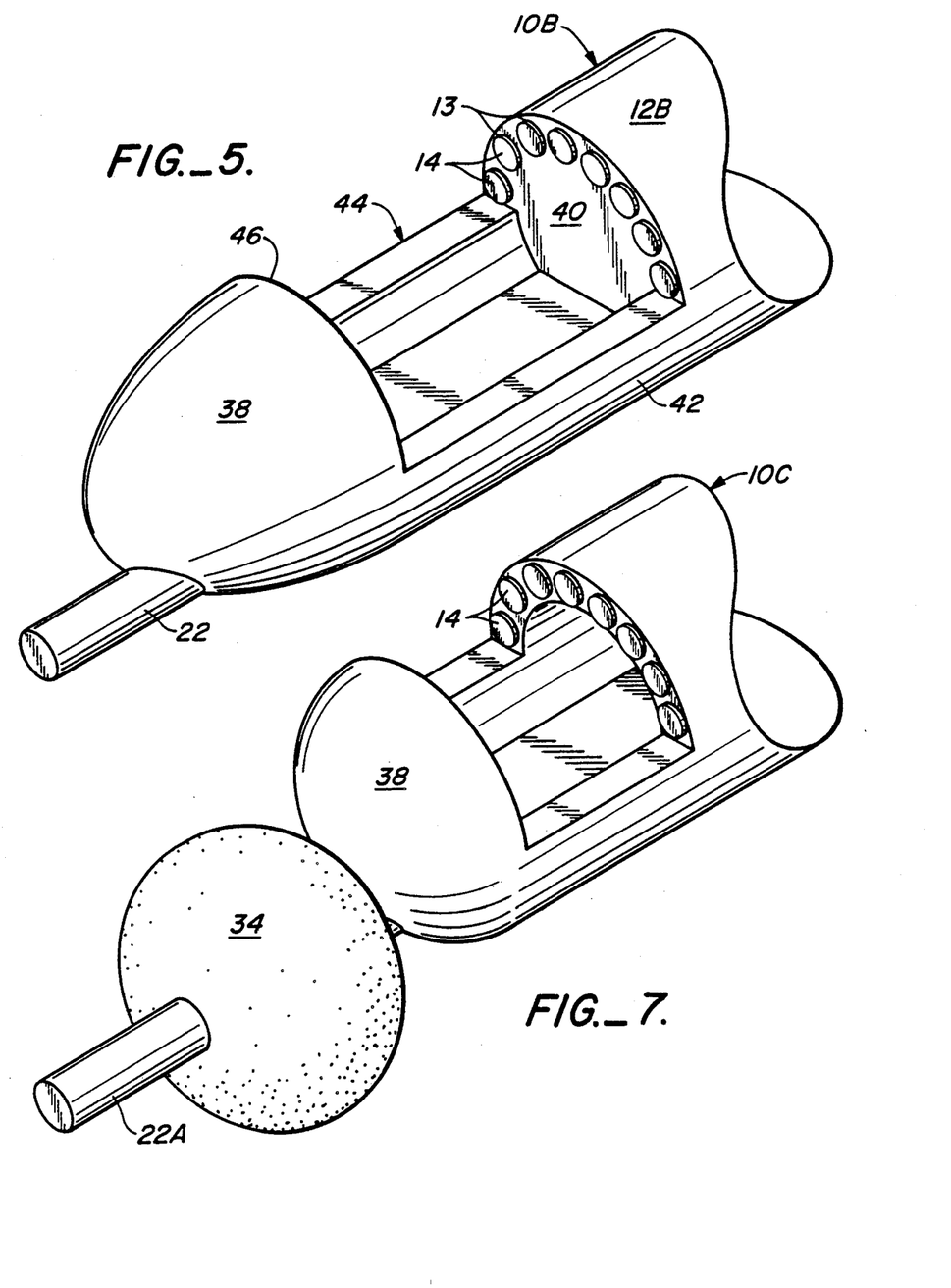
FIG. 5 is an enlarged fragmentary view in perspective showing the distal end of another form of catheter embodying principles of the present invention.
FIG. 7 is an enlarged fragmentary view in perspective showing the distal end of another form of catheter embodying principles of the invention.
Figure 5A:
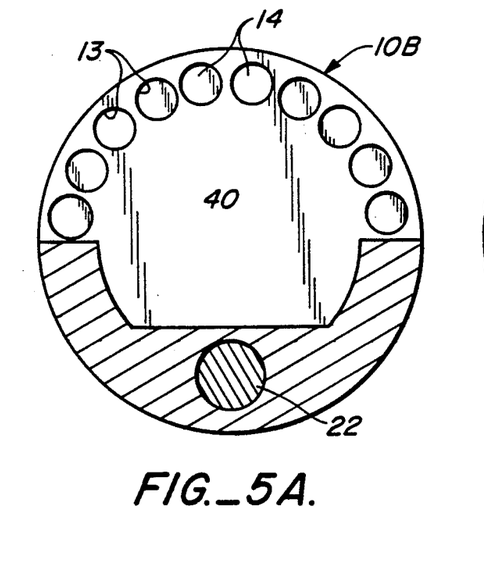
FIG. 5A is a view in section of the device of FIG. 5, taken along line 5A—5A of FIG. 6A.

In another modified form of the invention as shown in FIG. 5, a catheter body 10B is provided with a tapered nose portion 38 spaced from an arcuate end face 40 of the catheter and connected by a portion 42 of the catheter body to form an open compartment 44 at its distal end. The compartment is open on one side of the cylindrical catheter body and its length is preferably somewhat larger than the diameter of the catheter. The arcuate end face 40 of the catheter includes the exposed ends of a series of laser transmitting glass fibers 14. At the other end of the compartment and parallel to the end face 40 is an inner face 46 of the nose portion which has an arcuate indented notch 48 (See FIG.6A). Within the catheter body is a lumen 20B for supporting a movable guidewire 22 as in the previous embodiments.

The closely spaced glass fibers 14 in the catheter body 10B are also supported in separate lumens 13 and are longitudinally movable within these lumens.

Figure 6A:
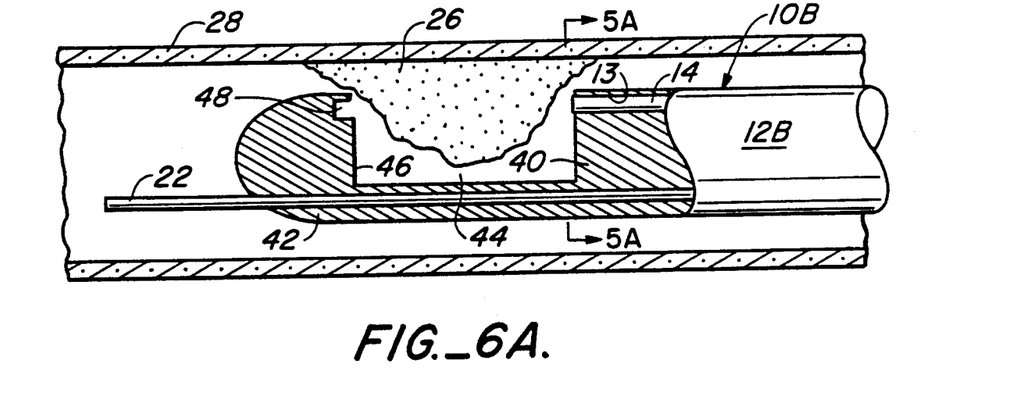
FIGS. 6A-6C are a series of elevation views in section showing the device of FIG. 5 as it appears during a typical operation within a body channel.
Figure 6B:
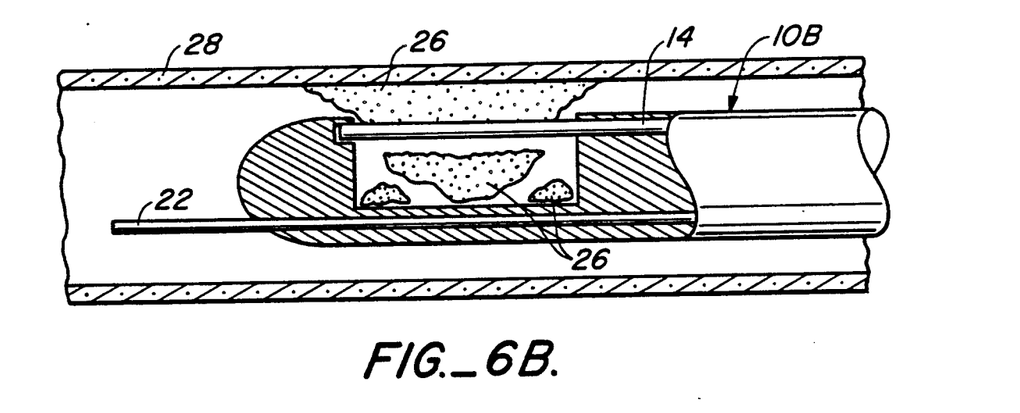
Figure 6C:
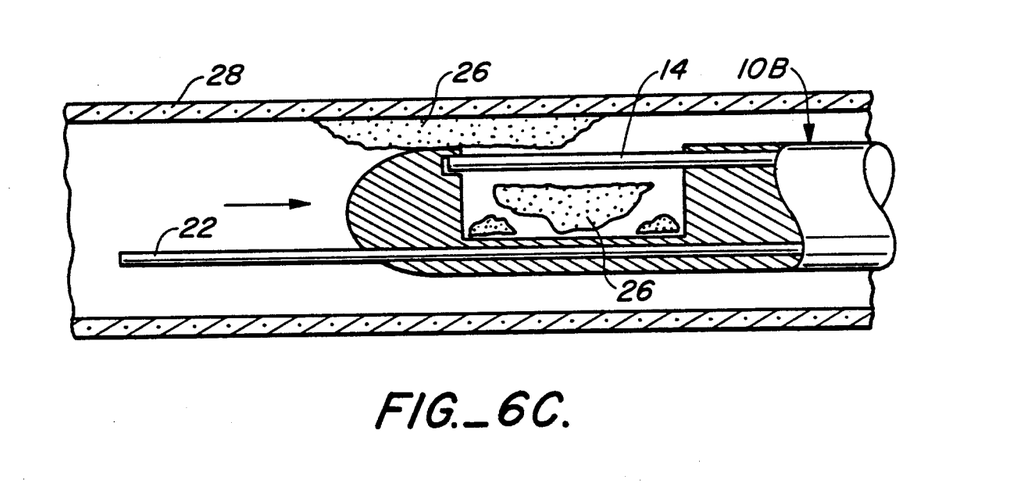

In the operation of catheter 10B, as shown in FIGS. 6A–6C, the guidewire 22 is installed in the conventional manner within the body channel being treated. As shown in FIG. 6A, the guidewire is first moved beyond the channel obstruction that is to be removed. Thereafter, the catheter 10B is installed on the guidewire, is moved along it and through the body channel until the distal end is positioned directly opposite the obstruction. Here the guidewire is offset to one side of the catheter body 12B which helps to maneuver the catheter nose portion 38 partially through the obstruction so that the main part of the obstruction material actually extends into the open compartment 44. With the catheter so situated, as shown in FIG. 6A, the fiber members 14 are simultaneously moved forward by an axial force applied to the fiber bundle at the proximal end as a laser energy source at its proximal end provides laser energy to the fibers. As the fibers 14 move forward, with pulses of laser energy being emitted from their ends, any obstruction material in their path is dissolved and/or severed as shown in FIG. 6B. When the movable fibers reach the arcuate slot 48 in the inner face of the catheter nose portion 38, the laser energy is turned off, and the severed obstruction material is retained within the compartment 44 which is now closed by the extended series of fibers 14. As shown in FIG. 6C, the catheter 10B with the severed and retained obstruction material and the guidewire 22 are now moved in the reversed direction to withdraw them from the patient's body channel. Again, the body channel obstruction has been removed with a combination of mechanical force and laser energy and a major portion of the severed obstruction material has been removed without allowing it to contaminate the blood or fluid in the body channel.

A somewhat modified catheter 10C similar to the catheter 10B is shown in FIG. 7 wherein a guidewire 22A having an inflatable element such as the balloon 34 is used. As previously described, the distal end of catheter 10C includes a tapered nose portion 38 with an open compartment 44 on one side which is closeable by a series of movable, laser transmitting glass fibers 14 in the catheter body 12C. The glass fibers are movable in unison from one inner end face 40 of the catheter compartment to the inner end face 46 of the nose portion 38 which forms the opposite end of the compartment.

Figure 8A:
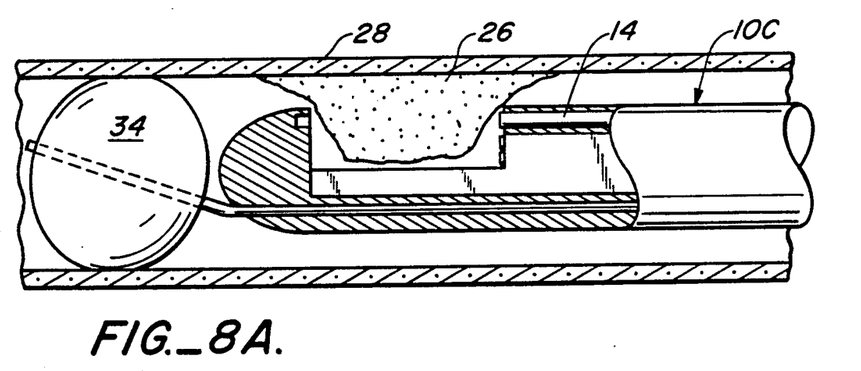
FIGS. 8A-8C are a series of elevation views in section showing the catheter of FIG. 7 as it appears during a typical operation within a body channel.
Figure 8B:
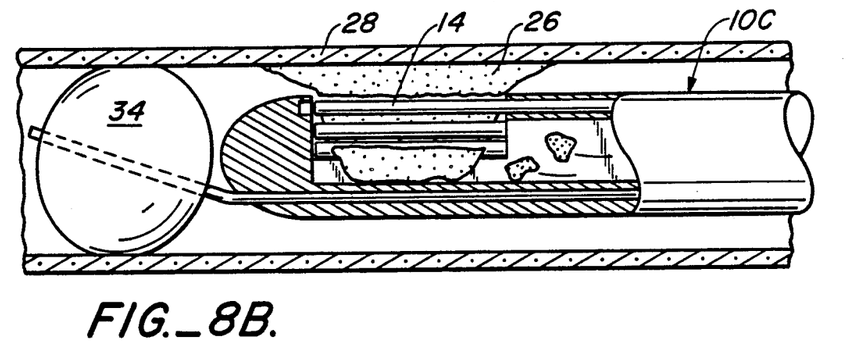
Figure 8C:
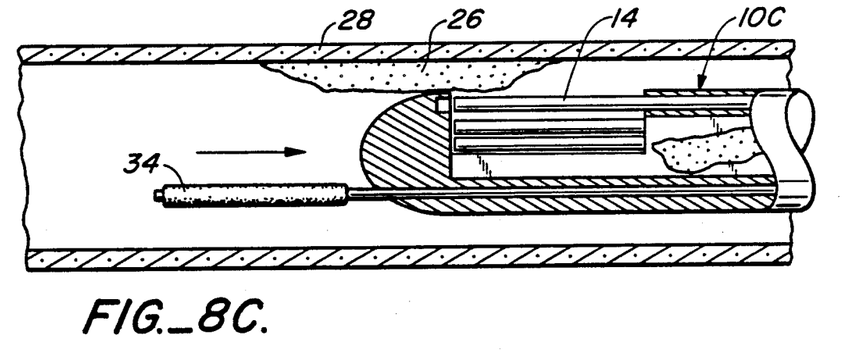

As shown in FIGS. 8A-8C, using the catheter 10C, the guidewire 22A is first installed and positioned within a body channel 28 so that the balloon 34 on the guidewire can be inflated just beyond an obstruction 26 located on one side of the body channel, as shown in FIG. 6A. Now, the catheter is moved along the guidewire until the open compartment 44 in the distal end of the catheter is directly opposite the channel obstruction 26. The catheter can be rotated on the guidewire 22A using the known technique so that the catheter is moved laterally closer to the obstruction and the latter projects well into the compartment 44. Now, as with catheter 10B, the fibers 14 are moved forwardly in unison at a slow rate as the laser source at the proximal end is energized and laser beams from the ends of the fibers dissolve and sever the obstruction material. The larger pieces of undissolved obstruction material fall into the compartment 44 and are trapped as the fibers reach the inner face of the nose portion. Thereafter, as shown in FIG. 8C, the balloon 34 is deflated, and the entire catheter assembly 10C with its guidewire 22A is carefully removed from the body channel or artery.

From the foregoing it is apparent that the present invention provides a unique catheter system that combines the use of mechanical force, such as dottering, with laser energy to remove obstructions or blockages in body channels with increased efficiency and safety. The combination of mechanical force as described serves to displace the obstructive material directly into the path of the laser beams which are thus highly effective in dissolving and/or severing the obstructive material. The invention also provides for the removal of severed material in lieu of allowing it to be carried away by the channel fluid adds a significant safety feature with respect to the prevention of future blockages in a patient.

The preferred embodiment described herein is intended to be purely illustrative, and not limiting of the scope of the invention. Other embodiments and variations will be apparent to those skilled in the art and may be made without departing form the essence and scope of the invention as defined in the following claims.

What is claimed is:

1. A catheter device for removing an obstruction in a human body channel, said device comprising:
   a catheter having an elongated body with a distal end portion adapted to be inserted within a channel and a proximal end portion, said catheter body comprising a forwardly extending tapered nose member at its distal end, said nose member having a large end whose diameter is smaller than the diameter of said catheter body, thereby forming an annular distal end face of said catheter body surrounding said large end of said nose member;
   a lumen extending lengthwise through said catheter body;
   a guidewire having a distal end extending through said catheter lumen and longitudinally through said nose member beyond the catheter's distal end;
   expandable means mounted on said guidewire near its distal end and means for controlling said expandable means at said proximal end portion;
   a series of fiber members extending through said catheter body, said fiber members being parallel and having distal ends that are closely spaced at said annular distal end face of said catheter and extending to its proximal end;
   laser means connected to said fiber members near the proximal end of said catheter for delivering laser energy through said fiber members and forwardly therefrom at said catheter end face.

2. A catheter device for removing an obstruction in a human body channel as described in claim 1 wherein said expandable means is a balloon, said guidewire including an air passage for said balloon to a proximal end.

3. A catheter device for removing an obstruction in a body passage as described in claim 1 wherein said fiber members are spaced apart circumferentially in a circular pattern completely around said catheter body at its distal end face.

4. A catheter device for removing an obstruction in a body passage as described in claim 1 wherein said fiber members are spaced apart by a distance no greater then one fiber diameter.

5. A catheter device for removing an obstruction in a body passage as described in claim 1 wherein said conical nose member has a length that is approximately three times its maximum diameter at an inner end.

6. A catheter device for removing an obstruction in a body passage as described in claim 1 wherein said fiber members are of glass material having a diameter in the range of 1-600 microns.

7. A catheter device for removing an obstruction in a human body channel, said device comprising:
   a catheter having an elongated body with a distal end portion adapted to be inserted within a channel and a proximal end portion;
   a lumen extending lengthwise through said catheter body;
   a guidewire having a distal end extending through said catheter lumen and beyond the catheter's distal end;
   expandable means mounted on said guidewire near its distal end and means for controlling said expandable means at said proximal end portion;
   a series of fiber members extending though said catheter body, said fiber members being parallel and closely spaced near a distal end face of said catheter and extending to its proximal end;
   laser means connected to said fiber members near the proximal end of said catheter for delivering laser energy through said fiber members and forwardly therefrom at said catheter end face; and
   wherein said catheter body comprises an annular outer portion containing said fiber members and forming a central bore and a tubular lumen within said central bore for said guidewire and a plurality of radial web members interconnecting said annular portion and said lumen.

8. The catheter device as described in claim 7 wherein said lumen for said guidewire within said catheter body is fixed within said bore to the inner surface on one inner side of said annular outer portion.

9. The catheter device as described in claim 7 wherein said tubular lumen for said guidewire is concentric with said outer annular portion.

10. A catheter device for removing an obstruction in a human body channel, said device comprising:
    a catheter having an elongated body with a distal end portion adapted to be inserted within a channel and a proximal end portion;

a lumen extending lengthwise through said catheter body;

a guidewire having a distal end extending through said catheter lumen and beyond the catheter's distal end;

expandable means mounted on said guidewire near its distal end and means for controlling said expandable means at said proximal end portion;

a series of fiber members extending through said catheter body, said fiber members being parallel and closely spaced near a distal end face of said catheter and extending to its proximal end;

laser means connected to said fiber members near the proximal end of said catheter for delivering laser energy through said fiber members and forwardly therefrom at said catheter end face; and wherein said distal end portion of said catheter body has an open compartment on one side defined by an outer transverse face spaced from an inner transverse face, a tapered nose portion on said body extending forwardly from said outer face and a narrowed body portion interconnecting said inner and outer faces, said fiber members terminating at spaced apart locations on said inner face and means at said proximal end for moving said fiber members within said catheter body, so that the distal ends of said fiber members can be moved forwardly from said inner face to said outer face as said laser means is activated.

11. A catheter device for removing an obstruction in a body passage as described in claim 10 including an arcuate groove in said outer face of said catheter compartment for receiving the distal ends of said fiber members when they have been moved forwardly from said inner face.

12. A catheter device for removing an obstruction in a human body channel, said device comprising:

a catheter having an elongated body with a distal end adapted to be inserted within a channel and a proximal end, a forwardly extending tapered nose member having a large end attached to said distal end portion of said body and a smaller distal end;

a lumen extending lengthwise through said catheter body and said nose member;

a guidewire having a distal end extending through said catheter lumen and beyond said nose member;

a series of fiber members extending through said catheter body, said fiber members being parallel to the longitudinal axis of said catheter body and terminating at spaced apart locations on an annular distal end face of said catheter surrounding the inner large end of said nose member, said fiber members extending to the proximal end of said catheter body and;

laser means connected to said fiber members near the proximal end of said catheter for delivering laser energy through said fiber members and forwardly therefrom at said circular distal catheter end face, whereby movement of said catheter body through a channel obstruction causes said nose member to mechanically force obstructing material radially outwardly toward the wall of said channel and closer to said annular end face of said catheter body so that laser energy directed through said fibers will impinge directly upon and dissolve said obstructive material.

13. A catheter device for removing an obstruction in a human body channel, said device comprising:

a catheter having an elongated body with a distal annular end portion surrounding a central bore and a proximal end portion;

a lumen extending lengthwise through said catheter body;

a guidewire having a distal end extending through said catheter lumen and beyond the catheter's distal end;

an inflatable bladder mounted on said guidewire near its distal end and means for controllably inflation said bladder at said proximal end portion;

a series of parallel, closely spaced fiber members extending within said annular end portion of said catheter body from a distal end face thereof to its proximal end;

laser means connected to said fiber members near the proximal end of said catheter for delivering laser energy through said fiber members and forwardly therefrom at said catheter end face in a cylindrical pattern, whereby as said laser means is activated to sever said obstructing material near the wall of said channel, said bladder is moved closer to said distal annular end portion of said body so that separated material is trapped and retained within said central bore.

14. A method for removing obstruction material from the internal side wall surface of a body channel comprising the steps of:

inserting a guidewire into said channel and moving it therethrough until its distal end extends beyond the obstruction material;

placing a catheter body having a tapered nose portion with a large end adjacent an annular end face of said body and a plurality of laser transmitting fiber elements along its length around said guidewire the distal ends of said fiber elements terminating at said annular end face surrounding the large end of said nose portion;

moving the catheter body along the guidewire through the channel until its said nose portion is adjacent the obstruction material;

advancing the catheter body slowly so t hat said nose portion will force the obstruction material closer to the internal wall of the channel while moving it closer to the distal ends of said laser transmitting element sin a position directly facing the obstruction material; and energizing a laser source to cause laser energy to be emitted from the distal ends of the transmitting elements into the obstructing material while continuing to advance the catheter body slowly.

15. A method for removing obstruction material from the internal side wall surface of a body channel comprising the steps of:

inserting a guidewire into said channel and moving it therethrough until its distal end extends beyond the obstruction material;

inflating a balloon near the end of said guidewire within the body channel;

providing a catheter body having an annular portion with a central bore supporting a series of laser transmitting fibers and a central lumen in the bore;

placing the catheter body around said guidewire and moving it along the guidewire through the body channel until it is positioned directly adjacent the obstructing material;

energizing a laser source at the proximal end of the catheter body to cause laser energy to be emitted from the distal ends of the fibers and into the obstructing material;

moving the catheter body forward slowly within the channel as the obstructing material is broken up; and moving the distal end of the catheter body through the obstruction material and closer to the balloon on the guidewire so as to trap portions of obstruction material in the central bore of the catheter body.

16. A method for removing obstruction material from the internal side wall surface of a body channel comprising the steps of:

inserting a guidewire into said channel and moving it therethrough until its distal end extends beyond the obstruction material;

providing a catheter body having a distal portion with an open compartment on one side and a plurality of fiber elements that terminate along an inner face of the compartment;

placing the catheter body around said guidewire and moving it thereon within the body channel until the open compartment is opposite the obstruction material;

moving the fiber elements within said catheter body from the inner face of the compartment to its other end so as to sever and retain portions of the obstruction material that extends into the compartment;

withdrawing the catheter body and guidewire from the body channel.

17. The method as set forth in claim 16 including the steps of:

providing an inflatable balloon near the distal end of said guidewire;

inflating the balloon after it has been positioned beyond the obstruction material.

turning and twisting the catheter body on said guidewire in order to move it closer to the channel wall and thereby forcing a substantial amount of the obstruction material into said compartment before said fiber members are activated and advanced to sever the obstruction material.

* * * * *